United States Patent [19]

Gorin et al.

[11] Patent Number: 5,077,017

[45] Date of Patent: Dec. 31, 1991

[54] INTEGRATED SERIAL DILUTION AND MIXING CARTRIDGE

[75] Inventors: Michael M. Gorin, Palo Alto; Robert S. Hillman, San Carlos; Ian Gibbons, Menlo Park; Michael E. Cobb, Sunnyvale, all of Calif.

[73] Assignee: Biotrack, Inc., Mountain View, Calif.

[21] Appl. No.: 117,791

[22] Filed: Nov. 5, 1987

[51] Int. Cl.⁵ .............................................. B01L 3/00
[52] U.S. Cl. ..................................... 422/100; 422/99; 422/102; 436/179
[58] Field of Search ................... 422/72, 99, 100, 102, 422/103; 436/176, 179, 180; 251/324, 326; 73/864.22

[56] References Cited

U.S. PATENT DOCUMENTS

| | | | |
|---|---|---|---|
| 1,740,004 | 12/1929 | Crowley | 251/324 |
| 2,326,487 | 8/1943 | Overbeke | 251/324 |
| 3,073,565 | 1/1963 | Daumy | 251/326 |
| 3,799,742 | 3/1974 | Coleman | 422/102 |
| 3,869,068 | 3/1975 | Chen . | |
| 4,503,012 | 3/1985 | Starr | 422/100 |
| 4,610,170 | 9/1986 | Ekholm et al. | 436/179 |
| 4,624,928 | 11/1986 | Qureshi | 436/179 |
| 4,758,409 | 7/1988 | Uffenheimer | 422/102 |
| 4,868,129 | 9/1989 | Gibbons et al. | 436/179 |
| 4,898,832 | 2/1990 | Klose et al. | 422/72 |

FOREIGN PATENT DOCUMENTS 0057110  4/1982  European Pat. Off. .
1163281  4/1969  United Kingdom .

Primary Examiner—Robert J. Warden
Assistant Examiner—D. John Griffith, Jr.
Attorney, Agent, or Firm—Richard L. Neeley

[57] ABSTRACT

A dilution and mixing cartridge comprising a sample application site, a mixing chamber in fluid receiving relationship to the sample application site, a diluent application site in fluid donating relationship to the mixing chamber, a first valve means selectively preventing flow from the diluent application site to the mixing chamber, and a mixture isolating chamber hydrostatically connected to the mixing chamber is provided along with a method for using this cartridge to sequentially dilute a sample with the same or different diluents.

20 Claims, 5 Drawing Sheets

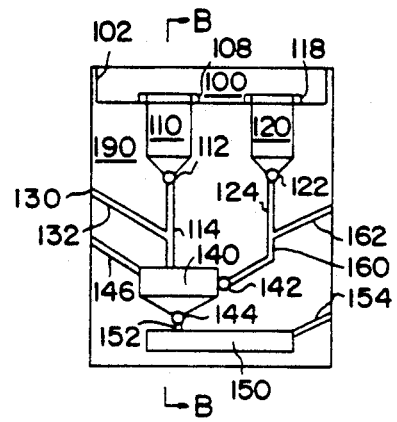
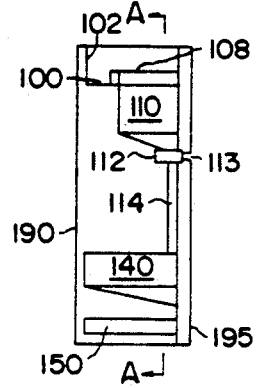
FIG.1A  FIG.1B
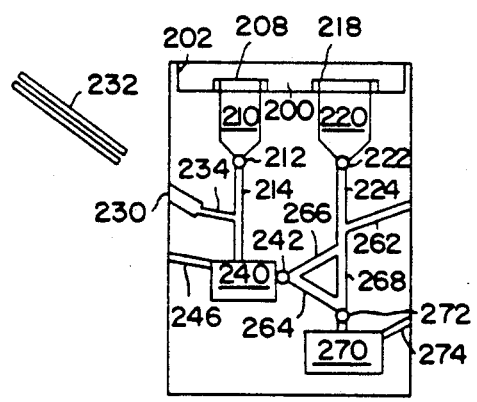
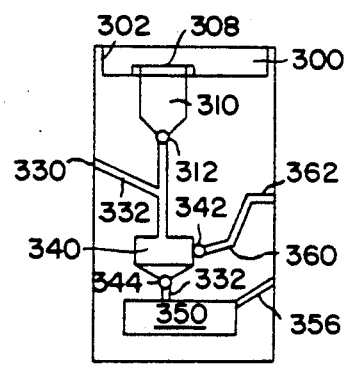
FIG.2  FIG.3
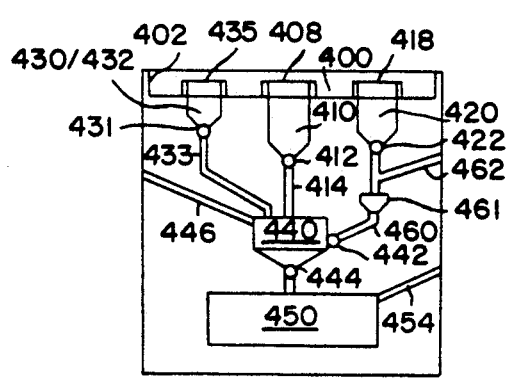
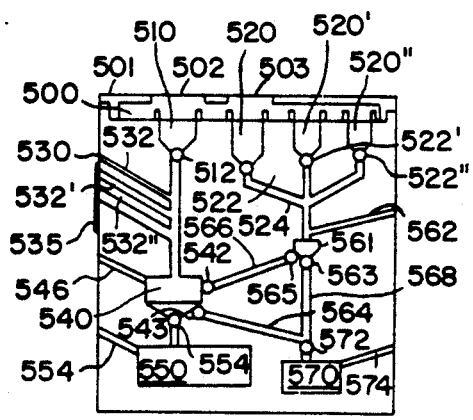
FIG.4  FIG.5

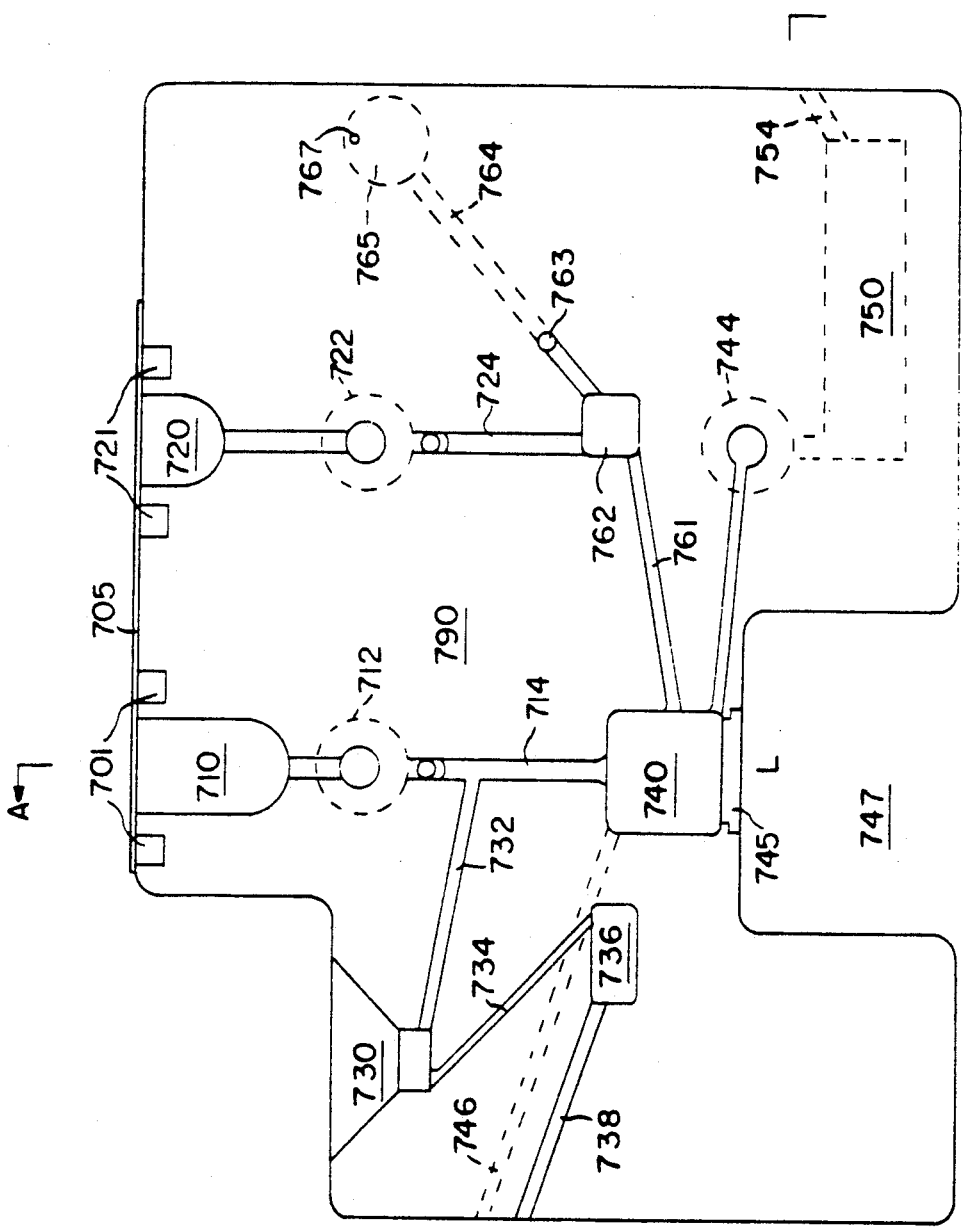
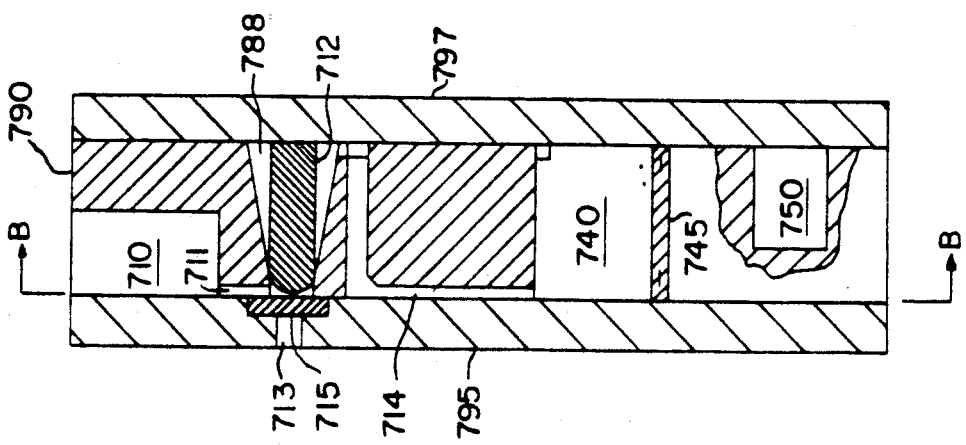
FIG. 12B
FIG. 12A

INTEGRATED SERIAL DILUTION AND MIXING CARTRIDGE

INTRODUCTION

1. Technical Field

This invention relates to methods and apparatuses used for diluting and mixing liquids, particularly the automatic measuring and diluting of small volumes of liquids.

2. Background

There has been a recent period of explosive growth in the field of clinical analyses intended to be carried out by unskilled users. Numerous approaches have been developed which allow an unskilled user, such as a diabetic patient, to determine the presence and/or amount of an analyte in a sample, such as glucose in urine. The devices that carry out such analyses are generally intended to be "user friendly" in that they require little training and are essentially fool-proof in use. Typical of these devices are the so-called "dipsticks". These devices are plastic strips with a reagent-containing matrix layered thereon. Sample is applied to the strip, and the presence or absence of an analyte is indicated by a color-forming reaction.

While such devices have proven useful for the qualitative determination of numerous substances in biological samples, not all analyses can be carried out in this manner. For example, some techniques require dilution and/or mixing of small quantities of sample. Measurement of extremely small amounts (e.g., microliter amounts) of liquid and the dilution thereof typically require significant training or the use of expensive equipment to carry out the dilution. Neither of these alternatives is convenient or easy to carry out.

Measuring and dilution of small samples of liquid is readily carried out in a number of automatic analyzers. However, these are not suitable for use in the home or in a doctor's office because of their size and expense. For example many devices are available in which a sample of liquid is drawn into a conduit which is in the form of a capillary tube that acts as a metering device. However, this metering device is part of a large apparatus containing pistons and numerous other moving parts, such as vacuum pumps, that are required for movement of the sample and diluent. The precision with which such moving parts must be manufactured in order to retain liquid-tight seals significantly increase the cost of the device.

As an alternative to large automatic analyzers, small hand-held micropipets, such as the well known Eppendorf® pipet, have been devised. These pipets utilize a precision piston to draw sample or diluent into a small disposable tip. However, skill is required in the use of the pipet, and a number of precise manual operations must be carried out to successfully measure sample and diluent. Skill is also required in mixing the resulting small-volume solution.

Another technique that has been developed for the home uses a capillary tube to measure a sample of fluid. The entire capillary tube is then placed into a large container which holds a measured quantity of diluent or to which a measured quantity of diluent is added. However, such devices are not generally satisfactory in the hands of an unskilled user, since capillary tubes are easily broken and since contamination of the outside of the capillary results in volume error.

Accordingly, there is a need for simple and accurate methods and devices for measuring, diluting, mixing, and analyzing small quantities of sample.

RELEVANT LITERATURE

West German published patent application DE3328964C1, publication date Feb. 14, 1985, describes a device for the automatic, discontinuous sampling of fluids using a capillary tube that acts as a measuring device and which can be either dipped into a fluid being sampled or alternatively moved into a position from which the sample is transported with a diluent to an analyzer by a pump or suction. U.S. Pat. No. 4,454,235 describes a capillary tube holder for liquid transfer in immunoassays. U.S. Pat. No. 4,233,029 describes a liquid transport device formed by opposed surfaces spaced apart a distance effective to provide capillary flow of liquid without providing any means to control the rate of capillary flow. U.S. Pat. Nos. 4,618,476 and 4,233,029 describe a similar capillary transport device having speed and meniscus control means. U.S. Pat. No. 4,426,451 describes another similar capillary transport device including means for stopping flow between two zones, flow being resumed by the application of an externally-generated pressure. U.S. Pat. Nos. 3,811,326; 3,992,150; 4,537,747; and 4,596,780 describe various processes and devices in which a capillary tube is used to take up a predetermined volume of the test solution and the charged capillary is in place in a cuvette or other container of liquid that is used as reagent or diluent. U.S. Pat. No. 3,799,742 describes an apparatus in which a change in surface character from hydrophilic to hydrophobic is used to stop flow of a small sample, thereby metering the sample present. U.S. Application Ser. No. 90,026, filed Aug. 27, 1987, describes an apparatus and method for automatic dilution of mixing samples, which does not contain moving valves but relies on capillary forces to stop flow between various internal chambers of a device.

SUMMARY OF THE INVENTION

The present invention provides a self-contained dilution apparatus that does not require the use of externally generated force (except gravity) to move liquids between its various parts and provide for reproducible dilution of samples. In particular, the apparatus provides for serial dilutions; i.e, dilution of a sample with a first diluent followed by dilution of the mixture with the same, a second, or a further diluent. The apparatus comprises a sample application site; a mixing chamber in fluid receiving relationship to the sample application site; a diluent application site in fluid donating relationship to the mixing chamber; a mixture isolating chamber hydrostatically connected to the mixing chamber; and first valve means selectively preventing flow from the diluent application site to the mixing chamber. Second valve means selectively preventing flow between the mixing chamber and the mixture isolating chamber can be provided as part of the device or by external control of venting of a capillary track. The parts of the device are integrated into a cartridge in which the valves are preferably actuated by external solenoids, which can be preprogrammed. In use, the mixing chamber of the device is supplied with a predetermined volume of sample and a predetermined volume of a first liquid diluent, thereby providing a first mixture. The device itself can be used to meter these volumes, if desired. A valve controlling passage of liquid from the mixing chamber to the hydrostatically connected mixture measuring chamber is opened, whereby a hydrostatically determined portion of the first mixture enters the mixture isolating chamber. The valve is then closed, isolating that portion of the first mixture from the remainder of the first mixture. This portion can then be transferred to a separate mixing chamber, or returned to the first mixing chamber, for dilution with a second diluent. Additional valves and chambers can be present if desired to provide for additional manipulation of the sample.

BRIEF DESCRIPTION OF THE DRAWINGS

The present invention will be better understood by reference to the following detailed description of the invention when considered in conjunction with the attached drawings that form a part of the present specification, wherein:

FIGS. 1A and B are vertical cross-sections of a first embodiment of the invention.

FIG. 2 is a vertical cross-section of a second embodiment of the invention in which an externally measured sample is added to the apparatus.

FIG. 3 is a vertical cross-section of a third embodiment of the invention.

FIG. 4 is a vertical cross-section of a fourth embodiment of the invention.

FIG. 5 is a vertical cross-section of a fifth embodiment of the invention.

FIGS. 12A and B are vertical cross-sections of a seventh embodiment of the invention.

DESCRIPTION OF SPECIFIC EMBODIMENTS

Figure 6:
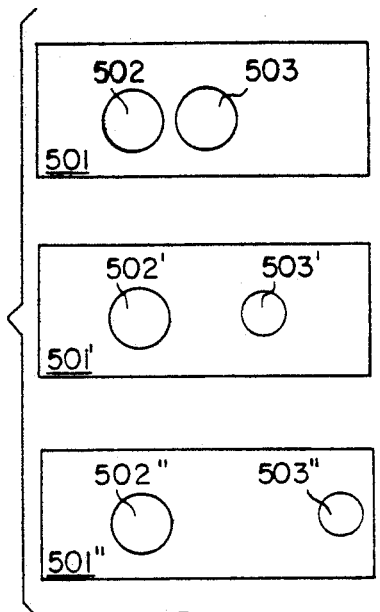
FIG. 6 is a plan view of three diluent application site covers for use with the embodiment of FIG. 5.

The present invention provides an apparatus and a method by which small samples can easily be measured and diluted. The apparatus is small, convenient to use, and requires no moving parts for the movement of fluid, gravity and capillary action being sufficient to provide all motive forces. Valves are provided to control the movement of fluid from chamber to chamber. The valves are integrated into the apparatus in most cases and, in preferred embodiments, are controlled by a simple push/release mechanism that can be controlled by an external solenoid. For some operations, valves can consist of externally controlled vent covers to control the flow of liquids in capillary spaces. Accordingly, the apparatus, referred to herein as a dilution and mixing cartridge, is easy to use, is inexpensive to manufacture, and can be used in a large number of procedures in which a dilution or a series of dilutions of a small sample is required.

The parts of the cartridge include a sample application site, a mixing chamber, a diluent application site, a mixture isolating and measuring chamber, and at least one valve controlling passage of fluid from the mixing chamber to the mixture isolating and measuring chamber. A second valve controlling passage of fluid from the diluent application site to the mixing chamber can be present as part of the cartridge or can be present as part of an apparatus into which the cartridge fits which operates a vent in the cartridge to control flow of a liquid in a capillary pathway. In some embodiments a sample measuring chamber will also be present. In contrast to the valveless apparatus described in U.S. patent application Ser. No. 90,026, filed Aug. 27, 1987, and discussed above, a variety of simple valves are provided for controlling passage of fluid between internal chambers of the device. These valves allow multiple use of the same chambers (e.g., serial dilutions a single mixing chamber) in contrast to the linear flow arrangement present in the previously described apparatus.

The various parts and the function of the various parts can be understood by following the course of action as a sample is applied to the apparatus and is diluted. The following description follows this plan of organization.

The sample is a liquid and may be derived from any source, such as a physiological fluid; e.g., blood, saliva, occular lens fluid, cerebral spinal fluid, pus, sweat, exudate, urine, milk, or the like. The liquid sample may be subjected to prior treatment, such as preparing serum or plasma from blood or dissolving or suspending a solid in a liquid. Examples of sample treatments prior to application to the apparatus of the invention include concentration, filtration, distillation, dialysis, inactivation of natural components, chromatography, and addition of reagents. In addition to physiological fluids, other liquid samples can be employed. Examples of other liquid samples include process streams, water, plant fluids, chemical reaction media, biological growth media, and the like. For the most part, the liquid will be aqueous, although other liquids can be employed. Aqueous media may contain additional miscible liquids, particularly oxygenated organic solvents, such as lower alkanols, dimethyl formamide, dimethyl sulfoxide, acetone, and the like. Usually the solvents will be present in less than about 40 vol %, more usually in less than about 20 vol %, in order to maintain the high surface tension that is present in aqueous solutions. However, the apparatus of the invention can be modified as described below for use with liquids exhibiting different surface tensions.

The sample application site will generally be a cavity on a surface of the apparatus or may simply be an opening (optionally surrounded by a ring or tube) leading to the interior of the apparatus. The sample application site can contain a filter, for example, to separate red blood cells from plasma (see U.S. application Ser. No. 924,633, filed Oct. 29, 1986), or may represent a connection between the apparatus of the invention and some other apparatus that manipulates the sample prior to its entering the present dilution apparatus. For example, the application site can be a recess into which a standard capillary tube will fit.

When the sample application site is a recess for insertion of a capillary tube, the capillary tube can act either as a convenient means for transferring the sample or can act as a measuring chamber, either by completely filling the capillary or by filling the capillary to a particular mark. The sample application site in such embodiments acts as a point of transfer.

In other cases, the sample application site will be a measuring chamber, such as a recess on an upper surface of the device into which sample is inserted. The application site can be provided with a raised lip surrounded by a catch basin so that the application site can be filled to overflowing, with excess sample overflowing into the catch basin. A defined volume of sample can therefore be readily obtained.

In still other cases, the sample application site can be a chamber having two channels leading away from the chamber. The first channel is or leads to an internal sample measuring chamber as described herein. The second channel is a drain that leads to an excess sample chamber. The excess sample channel is smaller than the measuring channel or is otherwise provided with means to restrict flow through the excess sample channel so that sample applied to the sample application site will flow primarily into the measuring chamber until the measuring chamber is filled, after which excess sample is drained away by the excess sample channel.

When sample is applied to the sample application site and the apparatus contains an internal sample measuring chamber, the liquid sample flows without the application of external force (except unassisted gravity) into the sample measuring chamber, which has a fixed volume. A capillary channel or non-capillary channel capable of transporting fluid can connect the sample application site to the measuring chamber, or the capillary or other channel exiting the sample application site can itself be the measuring chamber. The measuring chamber can be a capillary channel or chamber, in which case capillary action will aid or in some cases provide all the force necessary for filling the measuring chamber with sample from the sample application site. Capillary channels and chambers will generally have at least one dimension perpendicular to the flowpath in the range 0.01 to 2.0 mm, more generally 0.1 to 1.0 mm. However, larger measuring chambers are also possible. The sample measuring chamber is said to be in "fluid receiving relationship" to the sample application site in order to indicate that unassisted flow occurs.

The geometry of the measuring chamber is such that when diluent is added to the apparatus at a later step, essentially all of the sample in the measuring chamber will be expelled or drawn into the mixing chamber. One means of accomplishing this is by providing for smooth flow of diluent through the measuring chamber. A straight tube open at both ends is thus a preferred embodiment for this type of measuring chamber. In preferred embodiments of this type, diluent enters the measuring chamber in a front across the entire cross-sectional area of flow. This helps avoid mixing of diluent with sample and passage of diluent through the measuring chamber without expelling essentially all of the sample, which can occur if a small stream of diluent enters into a broader cross-sectional area of the measuring chamber.

In an alternate and preferred embodiment, the sample measuring chamber can terminate at a junction leading into a passageway between the diluent application site and the mixing chamber, both of which are later described. Passage of moving diluent past the junction will serve to draw sample into the mixing chamber. The passageway can be narrowed at the location of the junction to assist in drawing sample into the passageway and thus into the mixing chamber. This embodiment is particularly useful when the sample measuring chamber is a simple tube connecting the sample application site to the passageway between the diluent application site and the mixing chamber.

When sample flows into an internal fixed volume measuring chamber, flow generally stops when sample reaches a stop flow junction, so called because it marks the junction between the early part of the fluid track in which sample flows freely and the later part of the fluid track into which sample does not normally flow until the user initiates the dilution process. Since the stop flow junction exists at the limit of the flowpath of the sample, it will be found at one end of the measuring chamber. In some cases, this same location will be the beginning of the mixing chamber (i.e., when the two chambers are directly connected). However, in other cases an additional channel may connect the stop flow junction to the mixing chamber.

It should be recognized that flow stop can occur both stably and metastably. A metastable flow stop is one in which flow stops on the macroscopic level but may resume without apparent cause after a time interval of a few seconds to a few minutes. Gradual creep of liquids along container walls or through microscopic or submicroscopic channels resulting from imperfections in the manufacturing process is believed to be the mechanism by which flow starts again once it has stopped. Additionally, small, undetectable vibrations (such as might be caused by persons walking near the apparatus or starting and stopping of nearby equipment, such as air-conditioning units) may also be sufficient to start flow in a metastable situation. However, there is no requirement of absolute stability since the apparatus is designed for addition of a diluent and eventual starting of flow at the stop flow junction. Accordingly, any flow stop which can be sustained for at least 10 seconds, preferably at least one minute, and more preferably at least five minutes, is sufficient for the purposes of this invention.

A stop flow junction is not a traditional valve as it has no moving parts. Rather, this junction relies on backpressure from the surface tension of the liquid sample to stop flow. This backpressure can be created in a number of ways. For example, backpressure is created when the cross-sectional area of the flowpath increases in a region in which there is contact between the liquid and the container walls (e.g., when a small tube enters a larger chamber or when the cross-sectional area of a channel increases). Greater backpressure and more consistent operation is achieved when the increase in cross-sectional area of the flowpath is abrupt rather than gradual, particularly when there is a break in capillarity in the sample flowpath. Imperfections in the container walls during gradual widening of chambers may cause liquid to "creep" more on one side than another, thereby avoiding the creation of backpressure. Liquid can also creep around corners when imperfections are present. Unbalanced forces will also be present when the junction is not horizontal. A horizontal junction, for example, occurs when a vertical tube enters the top horizontal surface of a chamber. If a horizontal tube enters a vertical wall of a container, a vertical junction is present, and the pressure at the bottom of the stop flow junction will be greater than the pressure at the top of the junction, due to hydrostatic pressure caused by the different heights of liquid. Nonetheless, non-horizontal stop flow junctions can be created by reducing the diameter of the smaller channel containing liquid as it enters the larger area, thereby reducing the difference in pressure between the upper and lower portions of the junction.

In many cases, the junction will be formed when a small-diameter measuring tube (i.e., measuring chamber) enters a larger receiving chamber. A small measuring chamber can enter the larger receiving chamber at a right angle or at an angle other than a right angle. The angle between the internal wall of the small tube and the surface of the chamber in the latter case will be different at different locations around the circumference of the junction.

U.S. Pat. No. 4,426,451, which is herein incorporated by reference, describes a number of stop flow junctions that it refers to as "meniscus control means" for use in a device in which there is capillary flow from one zone to another. The stop flow junctions described in that patent can be used in the apparatus of the present invention. However, the patent is not directed to stopping flow when the second zone is not a capillary zone. In contrast to the specific teachings of the patent, which indicate that the walls of the capillary chamber must gradually narrow and gradually expand in order to provide for flow stop, an abrupt widening has been found to be more effective in the practice of the present invention when the second chamber (here the receiving chamber) is not a capillary space. Although it is recognized that imperfections will exist on the molecular level, it is preferred that the junction be as sharp as possible from a macroscopic view point, approaching as closely as possible the ideal junction formed by the intersection of the plane (which can be curved) forming the walls of the measuring chamber with the plane forming the wall of the receiving chamber surface in which the stop flow junction is found. Maintaining a horizontal junction to avoid pressure differentials, reducing the area of the junction, changing the surface of the capillary so as to decrease the hydrophilic character (for aqueous solutions), providing smooth surfaces (rough surfaces encourage creep of liquid along the surface), and providing an abrupt change in cross-sectional area (preferably providing an angle between intersecting surfaces of about 90° or lower) all operate to prevent creep of liquid from one chamber to the other.

In general, for small (capillary-size) junctions, the backpressure will be controlled by the smallest radius of curvature assumed by the meniscus. For example, when a capillary tube with a circular cross-section enters a larger space so that liquid bulges out into the space under hydrostatic pressure, the meniscus will be approximately spherical, and the backpressure ($\Delta p$) is given by the Young-Laplace equation: $\Delta p = 2\gamma/R$, where $\gamma$ is the surface tension of the sample fluid and R is the radius of curvature. See, Miller and Neogi, "Interfacial Phenomena: Equilibrium and Dynamic Effects", Marcel Dekker, Inc., New York, 1985, and Davies and Riedeal "Interfacial Phenomena", 2nd Ed., Academic Press, New York, 1963. If the fluid meets the surface at an angle greater than 0°, this backpressure will be reduced by a geometric term. The radius, R, will change (become smaller) as the hydrostatic pressure increases, so that the backpressure and hydrostatic pressure balance. As hydrostatic pressure increases, R reaches a minimum value (maximum curvature) determined by the geometry of the device and the contact angle. The corresponding backpressure defines the maximum hydrostatic pressure sustainable by the stop flow junction.

Backpressure is also created when the surface that the liquid contacts changes to decrease adhesion between the liquid and the container wall (for example, when an aqueous sample moves from a hydrophilic to a hydrophobic surface). The surface properties of the various interior surfaces of the device of the invention can and generally will be controlled by various physical and/or chemical treatments. For a discussion of controlling surface properties of similar devices, see commonly assigned U.S. application Ser. No. 880,793, filed July 1, 1986. For example, plastic surfaces can be treated to increase their hydrophilicity. Either the whole apparatus or specific parts can be treated. Alternatively, different parts of the apparatus can be made of different plastics. For capillary flow, contact angles of 0°-90° are sufficient, preferably 10°-85° and most preferably 30°-60°. In order to provide these contact angles for aqueous samples, the capillary surfaces will be hydrophilic. For non-aqueous liquids, a hydrophobic surface would be appropriate. By using a combination of container wall geometry and surface wetability, a backpressure range of from 0 (no change in cross-sectional area or surface adhesion) to 20 cm $H_2O$ and higher can be achieved with water as the liquid. When the backpressure is 0, the location in question is not a stop flow junction. A stop flow junction occurs when there is sufficient backpressure to prevent the flow of sample past a particular point in the flowpath e.g., from the fixed volume measuring chamber to the fixed volume receiving chamber.

It is also possible to use a valve to control flow of sample from the sample measuring chamber to the mixing chamber. Measuring/application sites for sample can be provided as described later for diluent, and the exit of liquid from such application/measuring sites can be controlled by valves in the same manner.

The sample application site, diluent application site, sample measuring chamber, and mixing chamber can be as described in U.S. application Ser. No. 90,026, described above. However, the apparatus of the present invention will differ in that valves are present, for example controlling exit of waste fluid from the mixing chamber or entry of a portion of the mixed sample and diluent to a hydrostatically connected measuring chamber that samples and measures a portion of the mixture prepared in the mixing chamber. Additionally, other valves can be present in the apparatus of the present invention, such as a valve controlling flow of diluent from the diluent application site.

In certain embodiments of the invention, the mixing chamber can be used to determine the volume of diluent by providing a mixing chamber smaller than the diluent application site. In other cases, volume of diluent is determined by the volume of the diluent application site, in which case the mixing chamber has a volume at least as great as and usually larger than the combined volume of sample and diluent.

There are no particular restraints on the geometry of the mixing chamber other than that smooth fluid flow be provided for in order to prevent trapping of gas bubbles. Providing entry of sample and diluent into a lower portion of the receiving chamber and providing an upper surface of the receiving chamber that slopes upward toward the vent both aid in avoiding trapped bubbles. If the mixing chamber is larger than the combined volume of sample and diluent, the vent is preferably in the non-wetted upper portion of the mixing chamber.

The vent can merely be a small hole terminated by a stop flow junction in order to avoid exit of liquid from the device or can be a more sophisticated vent designed for gas exit without exit of liquid (e.g., a microporous, hydrophobic plug capable of passing air but not hydrophilic liquids). A vent or other means to allow exit of trapped air must be provided at every location in which the trapping of air would interfere with the passage of liquids between the various chambers and/or channels of the device.

Although there is no theoretical upper limit on the size of samples that can be measured and diluted in this first step (or later steps) using an apparatus of the invention, the method and apparatus are particularly suitable for measuring and diluting small quantities of liquids. Accordingly, the sample measuring chamber will generally have a volume of from 0.1 $\mu$L to 100 $\mu$L, preferably 1 $\mu$L to 30 $\mu$L, and most preferably 3 $\mu$L to 10 $\mu$L. The diluent application site or mixing chamber (whichever acts to limit diluent volume) generally has a volume of from 3 $\mu$L to 1000 $\mu$L, preferably 10 $\mu$L to 300 $\mu$L, and most preferably 30 $\mu$L to 100 $\mu$L, thereby providing dilution ratios of from $10^4$:1 to 3:1, preferably $10^3$:1 to 10:1, and most preferably 100:1 to 10:1. Channels through which capillary flow will take place will usually have opposing walls spaced in the range of about 0.01 mm to 2 mm, more usually about 0.1 mm to 1 mm. The capillary spaces can be tubular (which does not necessarily imply a circular cross-section but can be square or other regular shapes) or can represent the space formed by flat plates and side walls with the side walls being spaced further apart than a capillary distance. A tubular chamber with at least one flat side (e.g., a square cross-sectional area, a rectangle with adjacent sides differing in length by no more than a factor of 1:2 to 1:4, or a semicircular chamber) are preferred for ease of manufacture in cases where channels are being formed by the joining of two adjacent surfaces, one of which can be flat.

It should be recognized that statements in this specification indicating upper and lower limits of ranges are to be taken as individually designating a series of upper limits and a series of lower limits which can be utilized in any combination. For example, a typical upper limit and a preferred lower limit may be used in combination to define a range of intermediate preference.

Serial dilution and mixing capabilities are provided by a mixture measuring and isolating chamber hydrostatically connected to the mixing chamber, and a valve controlling passage of fluids from the mixing chamber to the mixture isolating chamber. The first dilution takes place as indicated above during which time the indicated valve is closed to prevent escape of liquid from the mixing chamber. After the first mixture is formed, the valve controlling flow to the mixture measuring chamber is opened and fluid flows from the mixing chamber under the influence of hydrostatic pressure and/or capillary attraction. The portion of the mixture isolating chamber into which the mixture flows is smaller in volume than the total volume of mixed sample and diluent. This volume is determined by the geometry of the chamber, the amount of hydrostatic pressure available from liquid in the mixing chamber, and any capillary forces that are present. Various geometries can be provided for the mixture isolating chamber depending on whether the intent is to carry out a second dilution in the original mixing chamber or to transport the isolated portion of the mixed sample and diluent to another location for further dilution and/or analysis. For example, the mixture isolating chamber can be a tube (which does not imply circular cross-section), at least a portion of which extends upwardly from the connecting point between the mixing chamber and the mixture measuring chamber. When the valve is open, the mixture flows into the mixture isolating chamber until the level of liquids in the two chambers becomes equal, thereby equalizing hydrostatic pressure (assuming that capillary action is negligible). After this portion of the mixture has been isolated by closing the valve, the remainder of the mixture can be drained from the mixing chamber by opening a second valve that leads to a waste fluid exit in the mixing chamber. After the second valve is closed, opening the first valve allows the isolated portion of the mixture to return to the mixing chamber. A second dilution can then take place in the mixing chamber.

Alternatively, a portion of the mixture measuring chamber can extend below the first valve, for example in a V or U shape, with another portion extending upward. Providing a third valve at the low point of the mixture measuring chamber allows the measured portion of the first mixture to be drained into a second mixing chamber. In this embodiment, there is no requirement for the waste fluid exit in the mixing chamber since there is no need to remove the remainder of the first diluted mixture from the first mixing chamber.

In either embodiment, the diameter of the measuring chamber can be of capillary dimensions so that capillary force is significant in determining the level to which mixture rises in the mixture measuring chamber. This height can readily be regulated by providing a vent or large diameter segment (such as a bubble chamber) to break capillarity.

The apparatus of the invention can be designed for use with a particular assay or can be designed and prepared as an apparatus in which multiple assays can be carried out, depending on the order in which various valves are opened and closed and the contents of the various diluents, which can contain reagents for the development of a detectable signal (e.g., a color reaction) that depends on the presence of an analyte in the sample.

Any type of valve that will control the passage of liquids between chambers and/or channels can be used in the apparatus of the present invention. Simple valves that can be actuated to move between an open and a closed position by the application and release of a simple external force are preferred.

Examples of such valves include resilient blocking members that are present in or adjacent to a liquid flowpath. For example, a resilient blocking member can be present in a converging or diverging pathway so that the narrow portion of the pathway is blocked by the resilient blocking member when the blocking member is in its normal position. Application of force in a direction generally away from the restricted portion of the flowpath and toward the wider portion of the flowpath will open the valve by moving the blocking member away from the narrow walls of the flowpath. Alternatively, a normally open valve can be provided which is blocked by movement of a resilient blocking member to a location that cuts off flow of liquid. Specific examples of such valves are set forth in more detail below.

Other examples of such valves include sliding pins closely engaging a channel that laterally traverses a fluid flowpath. The pin has a segment capable of obstructing flow through the flowpath when the pin is in a first position and a segment capable of allowing flow through the flowpath when the pin is in a second position. Examples of such pins include rectangular pins having a flowpath channel between two opposite faces of the pin, the flowpath channel being out of register when the block is in a closed position and in register with the principal flowpath when the block valve is open. Pins with circular cross-sections can be used by providing an obstructing segment of the pin that snugly engages the channel in which the pin fits and obstructs the flowpath when the pin is in a closed position. A smaller cross-sectional area (such as is present in the handle of a dumbbell) provides an annular flowpath around the smaller, central portion of the pin when the pin valve is in the open position.

A resilient member can be provided to bias the pin into either the closed or the open position. A force acting on the pin can then slide the pin to a second location so that the pin valve is in the alternate position.

In preferred embodiments, access for the application of an external force on the pin is provided so that the pin can be moved between its two positions. For example, a section of the pin that protrudes externally from the apparatus can be provided so that a force acting parallel to the sliding axis of the pin can move the pin from its first biased position to a second position by acting against the direction of the biasing force. Alternatively, an aperture leading from a face of the pin opposite the biasing force to the external environment can be provided. Externally applied pressure, such as from compressed air or a finger of an external apparatus that enters the aperture, can be used to slide the pin between its open and closed positions. A resilient seal can be provided to prevent loss of liquid through the aperture while allowing force to be applied to the pin. Such seals can also be provided for the resilient blocking members described above.

The valves that can be used as integral parts of a cartridge of the present invention are not limited to those specifically exemplified here. Rather, any valve can be used that can control the flow of liquids through small flowpaths, such as flexible walls of a flowpath that can be compressed to restrict flow of liquid through the flowpath. Additionally, a dissolvable barrier can be provided in instances where an initially closed valve will be opened once and then maintained in the open position.

It is also possible to provide an external valve. For example, a flowpath through which capillary flow occurs can be blocked by closing an external vent. When the external vent is closed, liquid cannot enter the capillary pathway because of air or other gases in the capillary pathway. Opening the vent allows liquid to enter the capillary pathway. If the vent is closed while liquid is contained in the capillary pathway, the isolated liquid can later be used for other manipulations.

Valves consisting of external vent controls can be used in any situation where flow occurs through a capillary pathway (so that trapped air is effective to control flow of liquids) and where no liquid is stored in the cartridge prior to use. In many cases it is desirable to store premeasured diluents (which can contain reagents) in the cartridge when the cartridge is delivered to an end user. Internal mechanical valves are preferred for such uses in order to prevent accidental leakage.

By providing valves that can be operated by a simple externally applied force, a cartridge-like device can be provided in which the valves are opened and closed in a predetermined manner by an analytical device into which the cartridge is inserted. This analytical device can contain various optical and/or other types of sensors for detecting the presence of liquids or analytes in various mixing and/or measuring chambers of the cartridge in addition to providing means for opening and closing the valves.

Reagents can be provided at various locations in a device of the invention. Incubation times can be controlled by either manual operation of valves or by a mechanically or electronically stored program in the device into which the cartridge is inserted. The program would control the order and timing of opening and closing valves. The programmed device would contain solenoids or other means for providing force to open and/or close valves. In embodiments in which flow through a capillary pathway is being controlled by the opening and closing of a vent, a movable sealing pad that is capable of closing the vent will form part of the external programmed device into which the cartridge is inserted.

A series of Figures is provided to illustrate a number of embodiments of the invention. The embodiments shown in the Figures are not intended to be comprehensive, and numerous other embodiments within the scope of the appended claims will be apparent to those of ordinary skill in the field of the invention.

FIG. 1A is a vertical cross-section of a first embodiment of the invention in which line A—A shows the location of the cross-sectional view in FIG. 1B. Line A—A in FIG. 1B, which is also a vertical cross-section of the first embodiment, shows the location of the view shown in FIG. 1A. Sample application site 130 is located in a side face of body member 190. Diluent application site 110 is a cavity in an upper face of block 190. Valve 112 prevents premature passage of diluent from diluent application site 110 through passageway 114 to mixing chamber 140. Sample measuring chamber 132 connects sample application site 130 to fluid passageway 114. A stop flow junction is present at the intersection of sample measuring chamber 132 and passage 114. Vent 146 allows air in mixing chamber 140 to exit from the chamber when sample and diluent enter the chamber. Valves 142 and 144 prevent premature exit of mixture from mixing chamber 140. Valve 142 controls passage of liquid between mixing chamber 140 and isolating chamber 160, which is a narrow channel sloping upward from valve 142. Valve 144 allows excess mixture to pass from mixing chamber 140 through waste liquid channel 152 to waste liquid container 150, which is connected by vent 154 to the external environment. Vent 162 allows entry of liquid from mixing chamber 140 into isolating chamber 160 when vent 142 is open. Second diluent application site 120 is controlled by valve 122 which selectively prevents diluent from flowing through connecting channel 124 into isolating chamber 160 and through valve 142 back into mixing chamber 140. Body member 190 is provided with a lip 102 around the perimeter of the body member to provide a space 100 that acts as a catch basin for excess diluent. Diluent is measured by filling diluent application sites 110 and/or 120 and allowing a small amount of diluent to overflow lip 108 or 118, respectively, and flow into lower catch basin space 100, thereby ensuring complete filling of the diluent application site (and therefore accurate measurement of diluent). An access channel 113 is provided for application of external pressure to valve 112 and resulting movement of the valve between open and closed positions. Details of exemplary valves are set forth in later Figures.

The apparatus of FIG. 1 can be used in the following manner, among others. A liquid sample, such as a drop of blood adhering to a finger after a finger stick, is touched to sample application site 130. A measured amount is drawn by capillary action into sample measuring chamber 132. Diluent is then added to diluent application site 110 until diluent overflows lip 108. Valve 112 is then opened to allow the measured amount of diluent in diluent application site 110 to flow through passage 114 into mixing chamber 140. As diluent flows past the stop flow junction at the junction of chamber 132 and passageway 114, the sample is drawn into the diluent. Valves 142 and 144 are both closed during this first mixing. Air that would otherwise be trapped in mixing chamber 140 exits through vent 146. Mixing in chamber 140 can be facilitated by including within the chamber a mixing bar or by rocking the complete apparatus back and forth.

Vent 142 is then opened to allow a hydrostatically controlled portion of the mixture to enter mixture isolation chamber 160. Mixture will rise into chamber 160 until hydrostatic and capillary forces are balanced. Valve 142 is then closed, isolating a portion of the mixture in chamber 160. The remainder of the mixture in chamber 140 is then drained through exit channel 152 into waste chamber 150 by opening valve 144. Valve 144 is closed and valve 142 is opened to allow reentry of the isolated mixture into mixing chamber 140. Diluent is then added to second diluent application site 120 and valve 122 is opened to allow dilution of the isolated portion of the mixture with the second diluent. By providing chambers of appropriate sizes, further dilution operations can be carried out by re-isolating a portion of the mixture in chamber 160 followed by addition of a third or further diluent.

Apparatuses of the invention can readily be made by forming all cavities and passageways in body member 190 as shown in FIG. 1B. A cover plate 195 is then used to form the internal cavities, with any access channels (such as access channel 113 shown for valve 112) or vents being provided in the cover panel as desired.

FIG. 2 shows a second embodiment of the invention in which a separate capillary tube 232 is provided for obtaining and/or measuring a sample. Sample application site 230 in this embodiment is a recess into which capillary tube 232 fits. Connecting channel 234 allows sample to pass into passageway 214. Many of the features in this embodiment are strictly analogous to the features of the embodiment shown in FIG. 1. Such features are identified by a reference number in which the last two digits of the reference number are identical to the last two digits of the reference number in FIG. 1. The first digit of the reference number identifies the particular Figure. For example, valve 212 in FIG. 2 is identical in function to valve 112 in FIG. 1. Accordingly, the remainder of the description of this and other Figures will be principally directed to the differences between embodiments.

Mixing chamber 240 of FIG. 2 differs from the mixing chamber of the embodiment shown in FIG. 1 in that no waste liquid exit is provided. Instead, a single dilution takes place in chamber 240 after which valve 242 is opened. Mixture flows under hydrostatic control into descending arm 264 of the sample isolating chamber of this embodiment and then upward into ascending channel 266 and/or vertical channel 268. Valve 242 is then closed and a second mixing operation occurs in chamber 270. Valve 272 is opened to allow sample to flow into second mixing chamber 270 after which valve 222 is opened to allow diluent in diluent application 220 to enter chamber 270. Providing a three-part isolation chamber in the manner shown in FIG. 2 prevents inadvertent retention of the first mixture in channel 264, which would be likely to occur if channel 266 were not present. Channel 266 provides access for air from vent 262 so that channel 264 can freely drain into second mixing chamber 270.

FIG. 3 shows an embodiment in which serial dilutions can take place using a single diluent application site. Isolation chamber 360 is connected to the external environment by vent 362 but is not itself connected to a second diluent application site. After sample and diluent from diluent application site 310 have entered mixing chamber 340 to form a first mixture, valve 342 is sequentially opened and closed to isolate a hydrostatically determined portion of the first mixture in chamber 360. Valve 344 is then opened to drain the remainder of the first mixture into waste liquid chamber 350, after which valve 344 is closed. Valve 342 is then reopened to allow the isolated portion of the first mixture in chamber 360 to reenter chamber 340. At some time after the closing of valve 312, a second diluent (or a second volume of the first diluent) is added to diluent application site 310. Valve 312 is then reopened to allow formation of a second mixture in mixing chamber 340. This operation can be repeated as often as desired or until the capacity of waste chamber 350 is exhausted.

FIG. 4 shows an embodiment of the invention in which the sample application site and sample measuring site are the same. Passage of sample from the sample application/measuring site 430/432 is controlled by valve 431. Sample passes through passageway 433 to mixing chamber 440 where it mixes with diluent from diluent application site 410. After mixing, valve 442 is sequentially opened and closed to isolate a portion of the first mixture in chamber 460. A bubble chamber (non-capillary space) 461 is provided to prevent capillarity from drawing excess liquid into chamber 460. The remaining parts of this embodiment and its mode of operation are as described for FIG. 1.

FIG. 5 shows a complex embodiment of the invention in which multiple analyses can be carried out, depending on the combination of sample application sites, diluent application sites, and valving operations. Multiple sample measuring chambers 532, 532' and 532" of different volumes are provided to allow for the measurement of different sizes of samples. Similarly, diluent application sites 520, 520' and 520" of different volumes can also be provided, each controlled respectively by valves 522, 522' and 522". Both a waste liquid chamber 550 and a second mixing chamber 570 are provided so that mixing (and subsequent measurements) can take place in either mixing chamber. Alternate isolating chambers are provided under the control of different valving systems. For example, once a first mixture has been formed in chamber 540, valve 542 can be opened while valve 543 remains closed. Channel 566 therefore acts independently of channels 564 and 568 to isolate a portion of the first mixture. Alternatively, valve 542 can remain closed while valves 543 and 563 are opened. Under these circumstances, channels 564 and 568 act as the mixture isolating chamber. After the remaining mixture in mixing chamber 540 is drained into waste liquid chamber 550, valves 543 and 563 are opened to allow the trapped portion of the first mixture to drain into second mixing chamber 570. Channel 566 is not needed in this sequence of steps, unlike the embodiment of FIG. 2, since draining chamber 540 allows vent 546 to supply air for the mixture trapped in channel 564.

By providing a multiple use cartridge, such as that shown in FIG. 5, different analyses can be carried out by selecting proper combinations of sample application sites and diluent application sites (to allow for different degrees of dilution) and by selecting diluents containing different reagents. In order to simplify use of the cartridge for a particular type of application, covers can be provided which allow access to only selected sample and/or diluent application sites. For example, FIG. 5 shows a sample application site cover 535, which can be, for example, tape applied to cover all but one of the sample application sites for a particular assay. Likewise, cover 501 allows access through channels 502 and 503 only to diluent application sites 510 and 520. As shown in FIG. 6, alternate covers can be provided for different analyses in which access channels are present in different locations to allow access to different diluent application sites.

Figure 7:
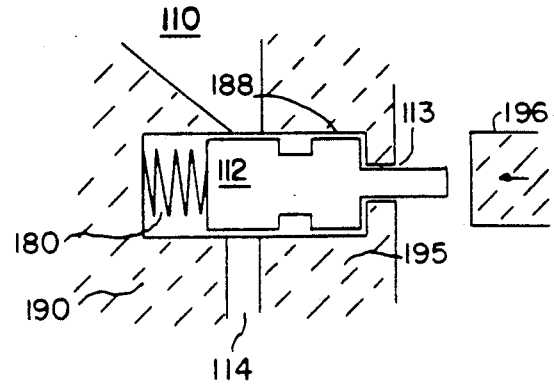
FIG. 7 is an expanded vertical cross-sectional view of a valve and the surrounding parts of the apparatus of FIG. 1A.

Although numerous types of valves can be used in an apparatus of the invention, particularly preferred embodiments are shown in FIGS. 7-10. FIG. 7 is a cross-sectional view of a valve such as might be present as valve 112 of the embodiment of FIG. 1. A channel 188 is present in the apparatus, which here is formed from base member 190 and cover plate 195. This channel traverses a flowpath of sample from diluent application site 110 to passageway 114 (which leads to mixing chamber 140). The valve shown in cross-section in FIG. 7 is shown in a perspective view in FIG. 8. The portion of the valve that slides in the channel consists of a cylindrical pin with sections having different diameters. An obstructing segment 182, snugly fitting channel 188, obstructs the passage of fluid from chamber 110 to passageway 114 when the pin is in the position shown in FIG. 7. The pin is maintained in this position by a resilient member 180, such as a spring, which presses outward on the body of valve 112. The depth of channel 188 in cover plate 195 is selected to retain pin 112 at the proper location. A projection 186 is provided on the end of pin 112 in order that an externally applied force operating parallel to and against the force produced by resilient member 180, which biases the valve into the closed position, can slide pin 112 in channel 188 to an open position in which segment 184 moves into the flowpath of liquid. Section 184 of pin 112 is of smaller diameter than segment 182 so that an annular flowpath of liquid is provided around the central portion of valve 112 at segment 184. For example, an actuating member 196, which is part of the apparatus into which the cartridge of the invention fits, can move in the direction shown by the arrow in FIG. 7 to act on protruding portion 186 of pin 112. When actuating member 196 contacts cover plate 195, thereby moving pin 112 to its maximum extent, valve 112 is in the maximum open position.

Figure 9:
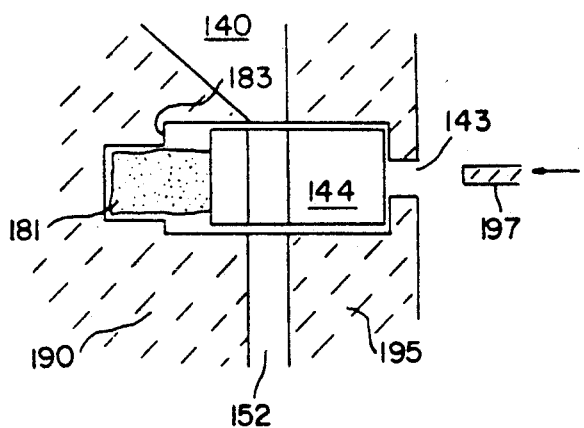
FIG. 9 is an expanded vertical cross-sectional view of a second embodiment of a valve of the apparatus of FIG. 1A.
Figure 10:
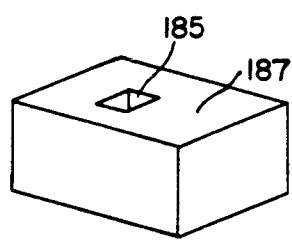
FIG. 10 is a perspective view of the valve of FIG. 9.

A second embodiment of a valve is shown in FIGS. 9 and 10 with FIG. 9 being a vertical cross-sectional view and FIG. 10 being a perspective view of the sliding pin. In this case the pin is rectangular with a channel 185 between opposite faces to allow passage of liquid. A portion of the same face 187 obstructs passage of liquid when the pin moves to the closed position. The valve of FIG. 9 differs from the valve of FIG. 7 in several ways. Pin 144 is biased by a foam pad 181 to a normally open position rather than a normally closed position. Access channel 143 is provided in cover plate 195, similar to access channel 113 of FIG. 7. However, no projection is provided on the face of pin 144. Instead, a pin 197 is provided as part of the analytical apparatus into which the cartridge fits. Pin 197 is located so as to enter channel 143 when moved in the direction shown by the arrow in FIG. 9. This embodiment provides easily actuated valves but avoids projections on the outer surface of the cartridge which might accidentally be triggered by handling. Channel 188 has shoulders 183 which prevent excessive movement of pin 144.

As indicated by the numbering system used, valve 144 of FIG. 9 is equivalent to valve 144 of FIG. 1. However, the valves of FIGS. 7 and 9 could be used at any location in the apparatus of the invention in which a valve is called for. In addition, many variations of valves of this type will be apparent to those skilled in the art from the description of the specific valves.

Figure 8:
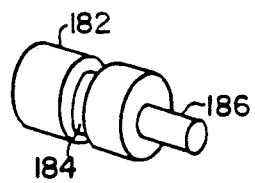
FIG. 8 is a perspective view of the valve of FIG. 7.
Figure 11:
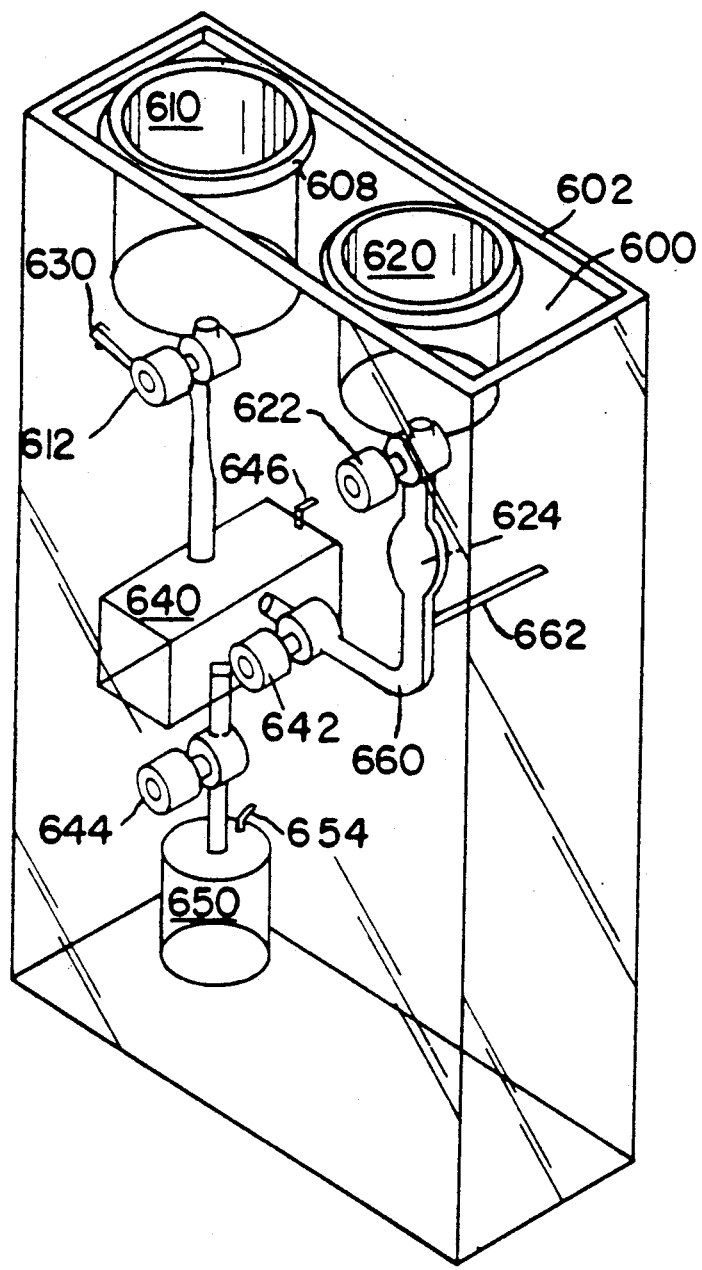
FIG. 11 is a perspective view of a sixth embodiment of the invention.

The Figures described above are not drawn to scale but are intended to indicate relative location and operation of some of the many possible variations of an apparatus of the invention. FIG. 11 is a perspective drawing in scale of an apparatus of the invention that resembles the device shown schematically in FIGS. 1A and 1B. The last two digits of the reference numbers correspond with the last two digits of the reference numbers in FIGS. 1A and 1B. Valves 612, 622, 642, and 644 are of the type shown in FIGS. 7 and 8 except that projection 186 of the pin shown in FIG. 8 is not present. Instead, the pin is contacted internally as shown in FIG. 9.

FIG. 12A is a vertical cross-section of a seventh embodiment of the invention in which line B—B shows the location of the cross-sectional view in FIG. 12B. Line A—A in FIG. 12B, which is also a vertical cross-section of the seventh embodiment, shows the location of the view shown in FIG. 12A. The device as shown is prepared from a base piece 790 and two cover plates 795 and 797. Most of the passageways and chambers are molded into base piece 790. Cover plate 795 contains apertures, such as aperture 713, through which force can be applied to operate internal valves, such as valve 712. In this embodiment, a resilient blocking member 712 is present in a channel 788 that diverges in the direction of the flowpath. The narrow end of channel 788 is blocked by one end of resilient blocking member 712, which is held in the blocking position by internal compression forces exerted when cover plate 797 traps blocking member 712 in channel 788. A resilient seal 715 is provided so that force can be applied through aperture 713 to blocking member 712 without leakage of sample or diluent from the device. Pressure on the end of resilient member 712 pushes it away from the narrow blocking portion of channel 788 toward the wider portion where flow can occur. In an actual device, resilient blocking member 712 could be approximately the size and shape of a thin lead pencil eraser and could be made of silicon rubber.

When valve 712 is open, diluent flows from chamber 710 through channel 711 along the front face of block 790 and then through 788 containing resilient blocking member (valve) 712. The flowpath continues into fluid passageway 714 at the rear of block 790 where liquid enters a channel traversing block 790 and then continuing across the front face of block 790 until liquid enters mixing chamber 740. Access panel 745 is provided to chamber 740 so that reagents can be added to the chamber during the manufacturing process, if desired.

Sample application site 730 is provided in an upper face of block 790. Two channels lead away from the sample application site. One channel is measuring chamber 732, which operates as described above for similar measuring chambers. An additional channel (734) is provided to remove excess sample from sample application site 730. Channel 734 is smaller than channel 732 so that sample initially flows preferentially into measuring channel 732. Excess sample channel 734 then leads excess sample into excess sample chamber 736, which is vented through vent 738 to the atmosphere. A measured volume of sample is therefore contained in channel 732 regardless of the amount of sample applied to application site 730.

Recess 747 is provided in a lower surface of block 790 immediately below chamber 740 in which mixing occurs. This recess allows close approach of a magnet or other means to activate a stirring bar or plate retained in chamber 740 while still allowing waste liquid chamber 750 to be located below (although displaced from) mixing chamber 740 in order that excess mixture an be readily drained into chamber 750.

In this seventh embodiment, a capillary pathway is provided for isolating a portion of the mixture initially formed in mixing chamber 740. Channel 761 along the front face of block 790 leads to a capillary space 762 to which a reagent can be applied before placing cover plate 795 over base 790. The capillary path proceeds to aperture 763, which traverses block 790. Capillary path 764 continues on the back face of block 790 and terminates at vent space 765 through back plate 795. Actual venting takes place through aperture 767 in back cover plate 797. A solenoid-controlled vent seal (not shown) forms part of the apparatus in which this embodiment is placed for controlling entry and exit of liquids into this capillary pathway. Capillary flow stops at the terminus of channel 764 when channel 764 enters vent space 765, which is non-capillary. The vent seal is then replaced, isolating a predetermined volume of mixture in the space formed by the entire capillary track (761–764). Liquid does not enter channel 724 because of air trapped in this space. After excess mixture is drained from mixing chamber 740, the vent seal (valve) is reopened to allow the isolated mixture to reenter mixing chamber 740. Diluent in chamber 720 further aids to expel trapped liquid in channel 761 and chamber 762 and to draw in trapped liquid from channels 763 nd 764 when valve 722 is opened.

Diluent chambers 710 and 720 are provided with a removable, sealable cover 705 that traps premeasured diluent in these chambers. Cover 705 is removed prior to use in order that flow can occur when valves 712 and 722 are opened. Optional catch spaces 701 and 721 are provided so that chamber 710 and/or 720 can be refilled with diluent, if desired.

Figure 13:
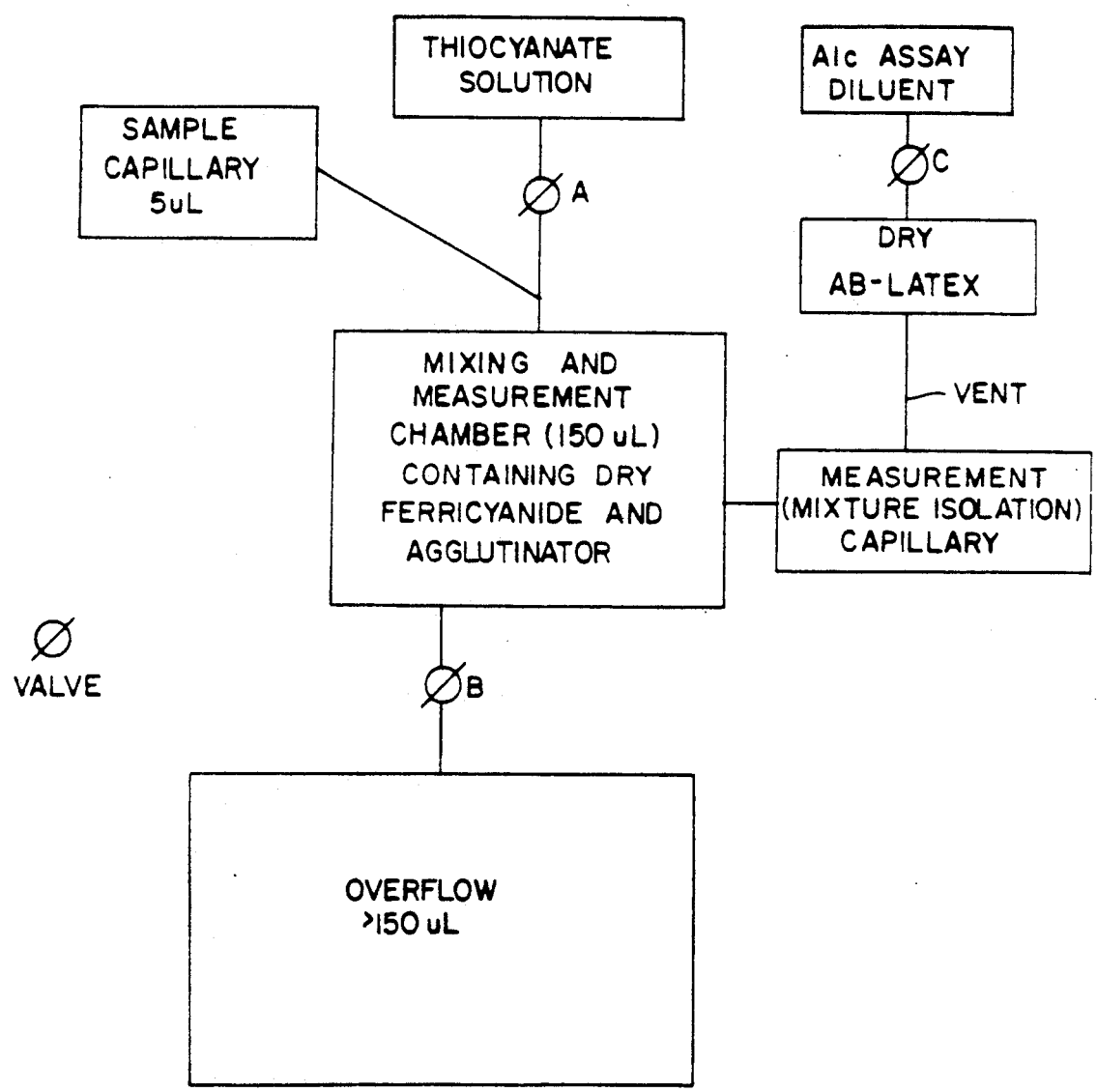
FIG. 13 is a schematic diagram of reagents and their location when using a device of FIGS. 12A and B to carry out an analysis of hemoglobin A1c.

FIG. 13 is a schematic diagram showing reagents that would be used with a cartridge of the type as shown in FIG. 12 to carry out a specific diagnosis. Hemoglobin A1c, a minor hemoglobin component, is present in normal persons but increases in the presence of hypoglycemia. Hemoglobin A1c measurement therefore provides an assessment of long-term insulin control in diabetics. An analysis requires an initial mixing of whole blood with a first set of reagents to determine total hemoglobin content followed by determination of hemoglobin A1c content on an aliquot of the first mixture. The process steps are shown schematically in FIG. 13. A sample from an unmeasured blood drop will be drawn into a sample capillary spontaneously. The sample size is defined by the volume of the sample capillary since flow of blood stops at the junction of the sample capillary and the pathway leading from the denaturant reservoir to the mixing/reading chamber. When valve A is open, thiocyanate solution will flow toward the mixing chamber, drawing the blood sample with it. The mixture of blood and thiocyanate will fill the mixing chamber, but liquid flow will stop when the mixture reaches an air vent (not shown in FIG. 13). Homogeneous mixing of blood and thiocyanate will now occur, driven by a reciprocating mixing plate, and the ferricyanide and agglutinator reagents present in the mixing chamber will dissolve. After about 1 minute, the blood will be lysed and the hemoglobin denatured. At this time, the total hemoglobin will be measured by reading absorbance at 540 nm and 800 nm using a light source and detector that are present in the device into which the cartridge has been inserted. Valve A will then be closed and the vent uncovered to allow a portion of the mixture to flow into the measurement (mixture isolation) capillary. The vent is then closed to prevent the isolated mixture from draining from the mixing chamber during the next step, in which valve B is opened so that all the remaining contents of the reaction chamber drain into the overflow chamber. Once the chamber has drained, valve B will be closed and valve C and the vent opened, allowing diluent to flow through the dry antibody-latex reagent chamber, resuspending the reagent, and displacing the sample of denatured blood (i.e., the isolated mixture) from the measurement capillary into the mixing/reaction chamber. The denatured blood/reagent mixture will then be mixed and assayed for hemoglobin A1c by measurement of the change in turbidity over about 30 seconds. Turbidity increases as a result of agglutination of antibody-coated latex particles, the antibody being specific for hemoglobin A1c.

The location of reagents described in FIG. 13 in the apparatus shown in FIGS. 12A and B is readily apparent. The sample capillary of FIG. 13 is measuring chamber 732 of FIG. 12B. Thiocyanate solution is present in chamber 710, A1c assay diluent in chamber 720, dry antibody-latex particles in chamber 762, and ferricyanide and agglutinator at different locations in chamber 740. Capillary channels 761–764 provide the measurement (mixture isolation) capillary with vent control occurring at vent chamber 765. Valves A, B, and C of FIG. 13 are respectively valves 712, 744, and 722 of FIG. 12B. The entire apparatus shown in FIGS. 12A and B would be approximately 2 inches high and less than 3 inches wide with body member 790 being 0.394 inch (1.00 cm) in thickness to provide a standard path length for spectrophotometric analysis of samples in chamber 740.

All publications and patent applications mentioned in this specification are indicative of the level of skill of those skilled in the art to which this invention pertains. All publications and patent applications are herein incorporated by reference to the same extent as if each individual publication or patent application was specifically and individually indicated to be incorporated by reference.

The invention now being fully described, it will be apparent to one of ordinary skill in the art that many changes and modifications can be made thereto without departing from the spirit or scope of the appended claims.

What is claimed is:

1. An apparatus for automatically carrying out a serial dilution of an aqueous sample with one or more aqueous diluents, comprising:
   a housing containing
   a sample application site for receiving a sample;
   a measuring chamber having a first volume;
   a mixing chamber having a second volume, wherein said second volume is greater than said first volume;
   a diluent application site for receiving a diluent;
   first flow means for delivering a sample from said sample application site to said measuring chamber by the sum of capillary and gravitational forces upon addition of sample to said sample application site;
   second flow means for delivering diluent from said diluent application site to said measuring chamber by the sum of capillary and gravitational forces upon addition of diluent to said diluent application site;
   third flow means for delivering sample and diluent from said measuring chamber to said mixing chamber by the sum of capillary and gravitational forces;
   a stop flow junction first located in said third flow means and adapted to the surface tension characteristics of the sample so as to provide sufficient back pressure resulting from contact between said sample and wall means of said housing at said stop flow junction first valve means to prevent sample from flowing through said stop flow junction first valve means in absence of diluent but allowing flow through said stop flow junction first valve means when diluent is present in said apparatus along with said sample;
   a mixture isolating chamber connected to said mixing chamber by a fourth flow means for delivering a portion of the contents of said mixing chamber to said mixture isolating chamber by the sum of capillary and gravitational forces; and
   normally closed first valve means selectively preventing flow between said mixing chamber and said mixture isolating chamber, whereby opening said first valve means causes a measured representative sample of a liquid in said mixing chamber to flow into said mixture isolating chamber.

2. The cartridge of claim 1, wherein said mixing chamber has an internal volume of no more than 1 ml.

3. The cartridge of claim 1, wherein said diluent application site comprises a depression in an upper surface of said cartridge and said upper face further comprises a catch basin surrounding said diluent application site.

4. The cartridge of claim 1, wherein said sample application site comprises a channel sized to receive a capillary tube.

5. The cartridge of claim 4, wherein said mixture isolating chamber is in fluid donating relationship to a second mixing chamber and further comprises second valve means selectively preventing flow from said mixture isolating chamber to said second mixing chamber.

6. The cartridge of claim 1, further comprising means for selectively draining said fluid chamber whereby a liquid in the mixing chamber may be drained and the measured representative sample from said mixture isolating chamber may be reintroduced into the mixing chamber.

7. The cartridge of claim 6, wherein the means for selectively draining said fluid mixing chamber comprises a waste chamber in fluid receiving relationship to said mixing chamber and a second valve means for selectively permitting flow from said mixing chamber to said waste chamber.

8. The cartridge of claim 6, further comprising a second diluent application site in fluid donating relationship to said fluid mixing chamber and second valve means selectively preventing flow from said second diluent application site to said fluid mixing chamber whereby the measured representative sample may be further diluted.

9. The cartridge of claim 8, wherein said second diluent application site is in fluid donating relationship to said mixture isolating chamber.

10. The cartridge of claim 1, wherein said cartridge comprises a base and one or more covers and at least one of said sites, chambers, and flow means is formed from a depression or aperture in said base when at least one of said covers is attached to said base.

11. The cartridge of claim 10, wherein said valve means are held in place by said cover.

12. The cartridge of claim 1, wherein said valve means comprises a displaceable resilient blocking member capable of obstructing a fluid flowpath.

13. The cartridge of claim 12, wherein said blocking member is biased to block said flowpath in the absence of externally applied forces.

14. The cartridge of claim 13, wherein a portion of said blocking member obstructs a blockable narrow section of a valve chamber in which said blocking member is located as a result of said resilient blocking member being compressed against a wall of said valve chamber opposite said narrow section.

15. The cartridge of claim 14, wherein said valve further comprises an access port sealed with a resilient seal through which an external force can be applied to said blocking member to move said blocking member away from said narrow section.

16. The cartridge of claim 1, wherein said valve means comprises a sliding pin engaging a channel laterally traversing a fluid flowpath, said pin being movable from a first position to a second position and comprising a segment capable of obstructing flow through said flowpath when said pin is in said first position and a segment capable of allowing flow through said flowpath when said pin is in said second position.

17. The cartridge of claim 16, wherein said pin comprises an obstructing segment and an intervening non-obstructing segment, said obstructing segment snugly engaging said channel and obstructing said flowpath when said pin is in said first position, said non-obstructing segment being narrower than said channel to allow passage of fluid through said pathway when said pin is in said second position.

18. The cartridge of claim 17, further comprising biasing means for biasing said pin in a biased position in the absence of external force on said pin, said biased position being either said first position or said second position.

19. The cartridge of claim 18, wherein said biasing means causes a portion of said pin to project beyond a surface of said cartridge.

20. The cartridge of claim 18, wherein when said pin is actuated by an external force on said portion acting against said biasing means, said pin moves to an anti-biased position, said anti-biased position being said second position when said biased position is said first position and said first position when said biased position is said second position.

* * * * *